(12) United States Patent
Deslauriers et al.

(10) Patent No.: US 11,419,953 B2
(45) Date of Patent: Aug. 23, 2022

(54) REDUCED METASTABLE COMPLEX MACROCYCLIC CONTRAST AGENTS

(71) Applicant: INVENTURE, LLC, Southbury, CT (US)

(72) Inventors: Richard Deslauriers, Woodbury, CT (US); Michael Milbocker, Holliston, MA (US)

(73) Assignee: Inventure, LLC, Southbury, CT (US)

( * ) Notice: Subject to any disclaimer, the term of this patent is extended or adjusted under 35 U.S.C. 154(b) by 0 days.

(21) Appl. No.: 17/534,232

(22) Filed: Nov. 23, 2021

(65) Prior Publication Data
US 2022/0080058 A1    Mar. 17, 2022

Related U.S. Application Data

(63) Continuation of application No. PCT/US2021/045555, filed on Aug. 11, 2021.

(60) Provisional application No. 63/144,299, filed on Feb. 1, 2021, provisional application No. 63/144,346, filed on Feb. 1, 2021, provisional application No. 63/144,291, filed on Feb. 1, 2021, provisional application No. 63/064,085, filed on Aug. 11, 2020.

(51) Int. Cl.
*A61K 49/10* (2006.01)
*A61K 49/18* (2006.01)

(52) U.S. Cl.
CPC ........ *A61K 49/108* (2013.01); *A61K 49/1806* (2013.01)

(58) Field of Classification Search
None
See application file for complete search history.

(56) References Cited

U.S. PATENT DOCUMENTS

| | | |
|---|---|---|
| 5,494,656 A | 2/1996 | Davies |
| 6,303,761 B1 | 10/2001 | Wang et al. |
| 7,012,140 B1 | 3/2006 | Sherry et al. |
| 2011/0274624 A1 | 11/2011 | Decuzzi et al. |
| 2018/0185521 A1* | 7/2018 | Deslauriers .......... A61K 49/105 |
| 2019/0269805 A1 | 9/2019 | Deslauriers et al. |

OTHER PUBLICATIONS

Alpoim et al. Determination of the number of inner-sphere water molecules in lanthanide(III) polyaminocarboxylate complexes. 1992 J. Chem. Soc. Dalton Trans. 3: 463-467. (Year: 1992).*
International Search Report dated Nov. 9, 2021 from corresponding International Patent Application No. PCT/US2021/045555, 2 pages.
Written Opinion dated Nov. 9, 2021 from corresponding International Patent Application No. PCT/US2021/045555, 3 pages.

* cited by examiner

*Primary Examiner* — Jennifer Lamberski
(74) *Attorney, Agent, or Firm* — Ruggiero, McAllister & McMahon LLC (57) ABSTRACT

Gadolinium based contrast agents (GCA) incorporating linear ligand chelation are fundamentally different from GCAs incorporating macrocyclic ligands. The macrocyclic\GCAs are synthesized by pathways characterized by the formation of a sequence of metastable complexes before obtaining the final stable complex. The synthesis of linear GCAs do not form metastable complexes. Commercial macrocyclic GCAs contain unstable metastable complexes. These metastable species are not regulated and quickly release free Gd3+ ions upon administration into the body. Gadolinium based contrast agents with near zero metastable species content and methods of synthesizing the same are disclosed. Gadolinium based contrast agents with long dissociation time in the body, and low free Gd3+ ion formation are obtained using a synthesis method which departs in novel ways from the traditional free Gd3+-based synthesis methods.

14 Claims, 9 Drawing Sheets

REDUCED METASTABLE COMPLEX MACROCYCLIC CONTRAST AGENTS

CROSS-REFERENCE TO RELATED APPLICATIONS

This application is a continuation of International patent application PCT/US21/45555, filed on Aug. 11, 2021, that claims priority to U.S. Provisional Application No. 63/064,085, filed Aug. 11, 2020, U.S. Provisional Application No. 63/144,291, filed Feb. 1, 2021, U.S. Provisional Application No. 63/144,346, filed Feb. 1, 2021, and U.S. Provisional Application No. 63/144,299, filed Feb. 1, 2021, the entire contents of each of which are incorporated by reference herein.

BACKGROUND OF THE DISCLOSURE

1. Field of the Disclosure

The present disclosure is directed to contrast agents with near zero metastable species content and methods of synthesizing the same.

2. Description of the Related Art

Gadolinium based contrast agents are injectables capable of enhancing a biologic image obtained by magnetic resonance imaging (MRI). MRI detects the nuclear magnetic resonance of the proton in the hydrogens contained in a molecule of water. Images are formed by spatially measuring the resonance, which varies by water density and tissue type. The image signal is derived from the spins of the protons, whose spin are preferentially aligned with a static magnetic, homogeneous field.

Figure 1:
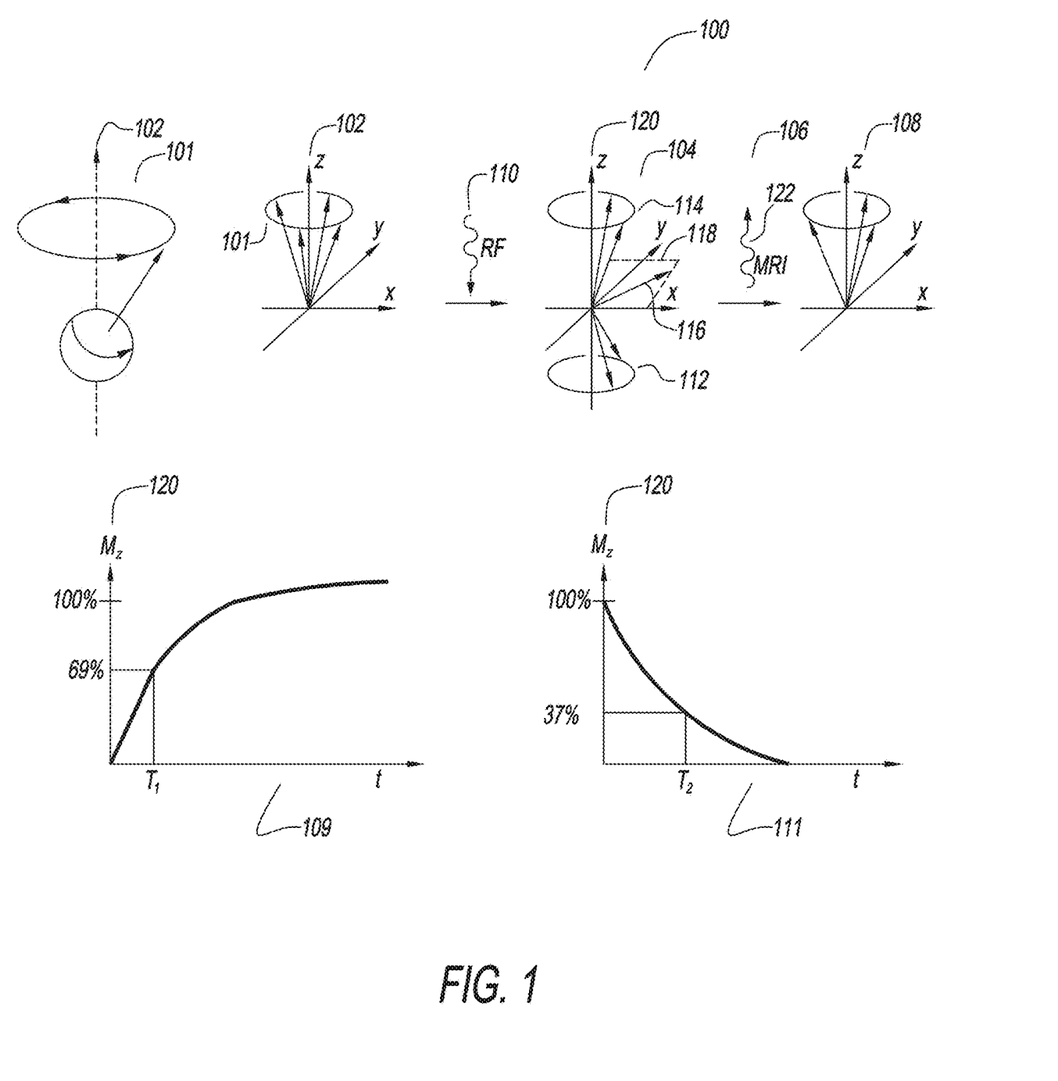
FIG. 1 provides a schematic of the dynamical proton spin during the MRI process.

The aligned protons are in a lower energy state than misaligned protons. When an RF pulse at resonant frequency (5-100 MHz) is applied to spin aligned protons, the low energy photons absorb that RF energy causing the proton spins to flip. Referring to FIG. 1, a schematic of the dynamical proton spin 101 during the MRI process 100 comprises alignment of proton spin with an external magnetic field 102, randomization of the alignment 104, and subsequent release of energy 106 comprising the signal of the MRI and return to the aligned state 108. The transition time from randomized state 104 to aligned state 108 is called the $T_1$ time 109. The transition time from the aligned state 102 to the randomized state 104 is called the $T_2$ time 111.

The $T_2$ signal involves absorption of the RF energy 110 by the aligned protons 102 which flips the proton spin 112. The combination of oriented 114 and counter-oriented 112 spins generates a combined spin vector in the xy-plane 116. The result is a spin moment vector 116 in the plane perpendicular 118, $M_{xy}$, to the direction of the magnetic field 120, $M_z$.

The $T_1$ signal involves emission of RF energy 122 by the spin randomized protons 104. When the RF pulse 110 stops, the proton spins relax back to their lower energy aligned state 102, releasing radio waves 122 comprising the image. The faster this transition occurs, $T_1$, the higher the intensity (energy per unit time) of the image signal.

Macrocyclic GCAs reduce $T_1$ and increase image quality by placing some of the protons of ambient water molecules inside a coordination cage. The coordination complex generates a reference frame for the protons. The equilibrium orientation of the complex is in the direction of the magnetic field, and the complex orientation is not randomized by the RF pulse. When the photon is energized by the RF pulse, it must resist the orientation of the coordination complex, which causes the spin to snap back to the aligned position faster than the protons of a free water molecule when the RF energy stops.

Coordination complexes are ubiquitous emergent structures with their own physical and chemical properties, many of which are confusingly complex. Coordination complexes are in a sense a distinct phase of matter, the molecular equivalent of the macroscopic crystalline state. The coordination complex results from the charge complementarity of a positively charged metal ion and the negatively charged groups of a ligand molecule.

The coordination complex is characteristically dynamical. The coordination bonds comprising the complex are reversible and metastable between covalent bonding and ionic bonding.

The atom within a ligand that is bonded to the central metal atom or ion is called the donor atom. In a typical coordination complex, a metal ion is bonded to several donor atoms. For example, a complex of $Gd3+$ ion and DOTA comprises 8 donor atoms, 4 of which are the nitrogen atoms of amine groups and 4 are the oxygen atoms of carboxylate groups. These complexes are called chelate complexes; the formation of such complexes is called chelation, complexation, and coordination.

Figure 2:
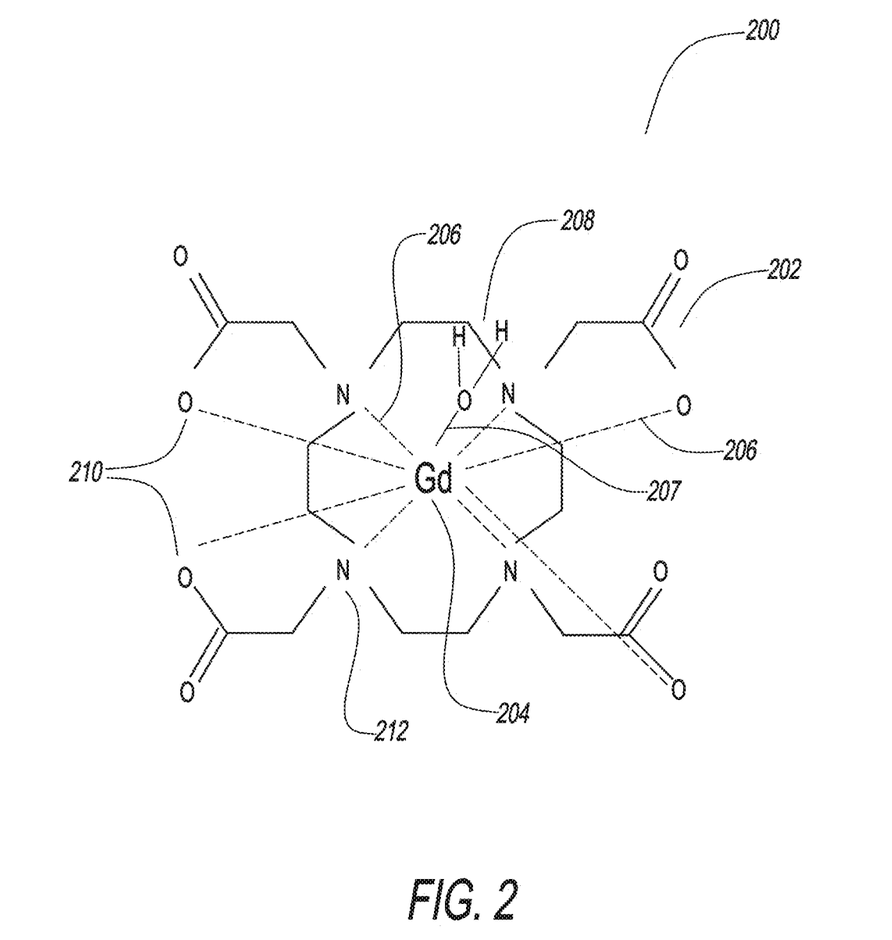
FIG. 2 depicts the gadoterate meglumine (Gd-dota) coordination complex.

Referring to FIG. 2, the gadoterate meglumine (Gd-dota) coordination complex 200 comprises ligand 202 (DOTA) and $Gd3+$ ion 204 and coordination bonds 206. Gadolinium has 9 possible coordination bonds, eight of which comprise the coordination bonds. The ninth bond 207 holds the $T_1$ reduced water molecule 208. This water molecule exchanges rapidly with ambient water without destabilizing the coordination complex 200. In this way, the Gd-dota complex can enhance the $T_1$ time for many water molecules. The coordination bonds are between the $Gd3+$ ion 204 and the oxygen atoms 210 of carboxylate groups on ligand 202 and the nitrogen atoms 212 of amine groups on ligand 202. Metastable forms of the coordination complex comprise states where one or more of the eight coordination bonds is broken and the negatively charged ligand groups 210 and 212 form bonds with the positively charged hydrogens of ambient water molecules. Before reaction of the ligand 202 with the metal ion 204 one or more of the ligand bonding sites 210 and 212 are occupied by water molecules. These water molecules are called hydration molecules. Formation of the coordination complex 200 involves removing these water molecules and replacing them with coordination sites on the $Gd3+$ ion 204. The hydration molecules of an metastable form complex do not participate in $T_1$ reduction since they are not centrally located and constrained by the enveloping effect of the ligand.

Figure 3:
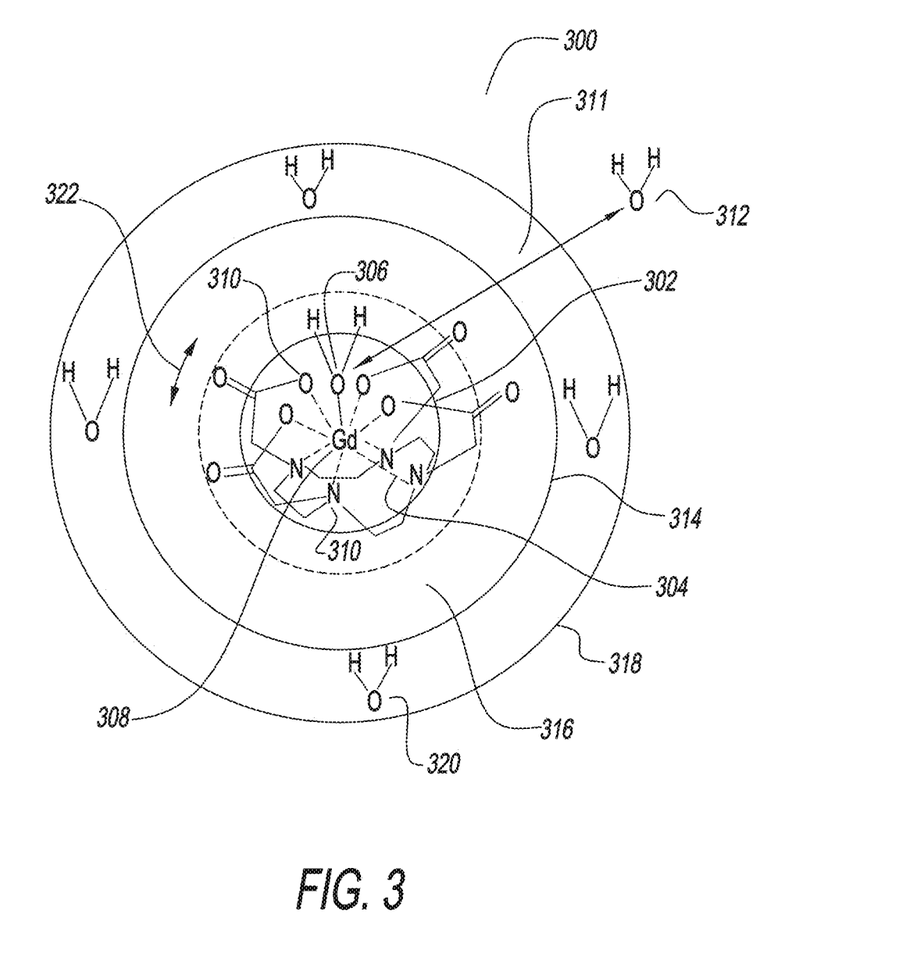
FIG. 3 depicts the gadolinium coordination sphere.

The central atom or ion, together with all ligands, comprise the coordination sphere. The central atoms or ion and the donor atoms comprise the first coordination sphere. Referring to FIG. 3, the coordination sphere 300 comprises first coordination sphere 302 which comprises the eight coordination bonds 304 between $Gd3+$ ion 308 and ligand groups 310, and the coordination water 306. The $Gd3+$ ion 308 resides centrally in the first coordination sphere 302. Coordination water 306 readily exchanges 311 with ambient water 312. The second sphere 314 comprises an outer region 316 where the $Gd3+$ ion 308 resides in the metastable complex state. The peripheral location of $Gd3+$ ion 308 is responsible for the instability of metastable complex states. A third outer sphere 318 comprising oriented water molecules 320 responsible for stabilizing the orientation of the coordinate complex 322.

Coordination refers to the "coordinate covalent bonds" (dipolar bonds) between the ligands and the central atom. By complex one means a reversible association of molecules, atoms, or ions through weak chemical bonds that are unique to the coordination phase of matter. The coordination aspect is usually more important than the complex aspect, and as such coordination complexes refer to a wide class of charge complimentary conformations where the bond strength varies from practically irreversible, to a collection of conformations embodied as a single dynamical coordination state. For example, several isomers of coordination configurations can comprise a single coordination complex. Consequently, formation of the coordinate complex, a subject of the present disclosure, depends sensitively on ambient reaction conditions, and several metastable forms are known. By metastable form of a given metal ion-ligand combination one means any coordination complex which is not the minimal energy coordination complex. The minimal energy coordination complex is called the final coordination complex. All metastable complexes are unstable and can dissociate to either the free ionic form or transform ultimately to the final coordination complex. When there is an energy barrier between the final coordination complex and an metastable coordination complex, generally the metastable coordinate complex degrades to the free ionic form. This energy barrier exists for the Gd-dota coordination complex and many other macrocyclic GCAs, and is primarily responsible for detectable levels of free Gd3+ ion in commercial macrocyclic GCAs.

The number of donor atoms attached to the central atom or ion is called the coordination number. A hydrated ion is one kind of a complex ion, and a species formed between a central metal ion and one or more surrounding ligands, molecules or ions that contain at least one lone pair of electrons. Metastable coordinate complexes contain hydrated ligand coordination groups.

A donor atom is an atom that gives a pair of electrons to a positively charged metal ion. There are some donor atoms or groups which can offer more than one pair of electrons. In some cases an atom or a group offers a pair of electrons to two similar or different central metal atoms or acceptors into a three-center two-electron bond. These types of exotic bonds which characterize uniquely coordination complexes are called bridging ligands.

The lanthanide series of elements, when hydrated, fall into a category called "hard" acids where bonding with other elements is considered largely ionic or electrostatic, even though these bonds are sometimes considered covalent.

Gd3+ ion is desirable as an image enhancement ion because of its favorable paramagnetic properties. However, Gd3+ ion is highly toxic. The toxicity of Gd3+ is due to its central position in the lanthanide series, with an ionic radius of 0.99 Å, very nearly equal to that of divalent Ca2+. This is one of the reasons why Gd3+ is so toxic in biological systems. Gd3+ competes with Ca2+ in all biological systems that require Ca2+ for proper function. The trivalent ion Gd+ binds with much higher affinity than the divalent ion Ca2+. When Gd3+ binds to a Ca2+ binding enzyme, the kinetics of the biological process catalyzed by that enzyme is severely compromised.

Gd3+ exists in aqueous solution in several hydration forms. Below pH 6 Gd3+ is hydrated with 8 or 9 first coordination sphere water molecules. Upon chelation by an organic ligand such as those used in clinically approved MRI contrast agents, the water molecules must be displaced from the first coordination sphere of the Gd3+ ion by the more basic donor atoms of the ligand, typically amines (N) or carboxylates (O). A typical ligand used to create MRI contrast agents has eight donor atoms. Upon chelation, a single water molecule remains in the first coordination sphere of the Gd3+. This single water binding site is important for MRI contrast because it allows, through chemical exchange, a large number of water molecules to have reduced $T_1$ time. When greater than one water molecule is present in the first coordination sphere the number of water molecules enhanced by $T_1$ reduction is significantly reduced. Interestingly, because metastable complexes are relatively rarely formed, typically less than 1% in the final product, the existence of metastable forms has been largely ignored. However, the propensity for metastable forms to release in vivo free Gd3+ ion makes the metastable forms a serious health threat at levels far below 1%.

SUMMARY OF THE DISCLOSURE

A novel understanding is required to appreciate the present disclosure involving novel changes to synthesis chemistry that accounts for the differences in the coordination chemistry of linear and macrocyclic chelates (ligands). The first consideration is the rate of complex formation. The rate at which a ligand forms a complex with $Gd(H2O)_8^{3+}$ depends upon many factors including pH, temperature, concentration of reactants and, interestingly, the structure of the ligand. The structure of the ligand determines the complexity of the reaction pathway toward a final coordination complex.

There are two structural classes of ligands, linear and macrocyclic. The structural differences between these ligands are why methods of synthesizing gadolinium contrast agents (GCA) of the past were based primarily on forming complexes with linear ligands. When these linear synthesis methods are applied to macrocyclic synthesis, including the reaction temperature, the reaction time, timing of raw material additions to the reactant, and diagnostic methods for determining when the synthesis product is obtained results in macrocyclic GCAs with high free in-bottle gadolinium and even larger potential free gadolinium. The reason free gadolinium can be more abundant for macrocyclic chelators of gadolinium is because the macrocyclics form less stable metastable complexes with gadolinium, whereas the linear ligands do not form metastable complexes.

Potentially free gadolinium refers to those metastable complex states which technically do not comprise free Gd3+ ion (and therefore are not detected as free), but readily release Gd3+ when introduced into the body.

Complex rate depends on pH, temperature and concentration of the ionic ligand and $Gd(H2O)_8^{3+}$ (Gd3+). The complex completion depends on driving the metastable complexes through a potential energy barrier separating the metastable and final complexes. Complex completion is not detectable with state of the art detection means, for example, xylenol orange titration. Xylenol orange titration is a method found in the USP guidelines which enable one to satisfy the free gadolinium safety limits. Clearly the limit is only as good as the detection means. Economic pressure to reduce synthesis time combined with ignoring the presence of metastable complex forms has resulted in synthesis methods which work against final complex formation. It should be appreciated that greater than 99% of the coordination complexes formed with the state of the art methods are the final coordination complex, the performance of the GCA with respect to MRI enhancement is unaffected. An object of the present disclosure is to employ novel methods and detection means which essentially reduces the presence of metastable complexes to zero, thus reducing the total amount of toxic free gad.

The variable which determines the correct values for these parameters is the structure of the free ligand. To understand the importance of the free ligand structure consider the canonical ligands of each structural type. The linear amine is diethylenetriamine pentaacetate (DTPA) and the cyclic amine is dodecane tetraacetic acid (DOTA).

DTPA is derived from the linear amine, diethylenediamine, by addition of five acetate groups. The resulting ligand is octadentate with three nitrogen donor atoms and five carboxylate oxygen donor atoms. The Gd3+ aqua ion is first attracted to the negatively charged carboxyl groups on DTPA by electrostatic attraction but the multidentate ligand is conformationally flexible so, once the Gd3+ ion is in the vicinity of the ligand, it rapidly wraps around the Gd3+ aqua ion and displaces all but one first coordination sphere water molecule.

This wrapping action is absent in the macrocyclic complexation. The wrapping action of linear ligands always excludes all but one of the 8-9 first coordination sphere water molecules, whereas the macrocyclics rely on thermodynamic parameters to complete the complexation. In other words, synthesis of macrocyclic GCAs involves relatively stable metastable forms with greater than one first coordination sphere water molecule.

Control of the thermodynamic parameters involves the novel synthesis of the present disclosure, and produces the novel metastable-free final coordination complex. By metastable-free one means a GCA with fewer than 1 metastable in $10^6$ GCA molecules. The GCA molecule being the maximally stable final complex.

Assuming the Gd3+ ion must be proximal to a ligand in order to form a coordination complex, then the time required to fully form the final thermodynamically stable product depends, to some extent, on the number of protons on the ligand (hence, the pH). Macrocyclic chelation times are typically long.

By way of comparison, the linear ligands form Gd3+ complexes faster than macrocyclic ligands. For linear ligands, the complex is fully formed on the order of a few hundred milliseconds to several seconds. In contrast macrocyclic amines, for example DOTA, involve metastable chelated forms which are thermodynamically unstable. Thus the reaction is not unidirectional toward the final coordination complex, as it is for linear GCAs.

The complex formation of Gd3+ ion with DOTA takes place in two steps: first, there is rapid formation of an metastable species in which the metal ion is incompletely coordinated and, afterwards, there is a slow rearrangement of this metastable into the final complex. The synthesis process can be further complicated by the traditional use of solvents to extract and dry the drug product. These solvents can form associations with metastable forms that are generally identified as contaminants, and must be reduced to levels allowed by regulatory bodies.

DOTA is derived from the macrocyclic tetraamine, cyclen, by addition of four acetate side arms. The resulting ligand is octadentate (like DTPA) consisting of four nitrogen donor atoms and four carboxylate oxygen donor atoms. The Gd3+ aqua ion is first attracted to the negatively charged carboxyl groups on DOTA by electrostatic attractions and the first product formed is an unstable metastable chelation. These metastables are not so unstable as to be detected by standard free gadolinium detection means, e.g., the xylenol orange test. However, in the presence of competing calcium ions the metastable complex becomes sufficiently unstable to dissociate in vivo. The resulting free Gd3+ ion is toxic.

The metastable formation comprises four carboxylates coordinated to the Gd3+ ion and 4-5 water molecules remaining in the coordination sphere. The presence of these water molecules result in the Gd3+ ion being situated further from the center of the coordination sphere, and with fewer ionic bonds between the ligand and the Gd+ ion.

Also, the macrocyclic amine portion of the molecule is conformationally rigid so the reaction temperature is important. The temperature threshold required to maximally reduce the ligand rigidity is a novel teaching of the present disclosure. Also, it takes more time for the Gd3+ ion to be completely encapsulated by the ligand, so the synthesis duration is also important.

Temperature and synthesis duration comprise two aspects of the reaction necessary to drive the complexation to completion. Heretofore, the role temperature and synthesis duration play with respect to driving the metastables to full complexes has not been appreciated. Lower temperatures and shorter synthesis times result in low measurable free Gd3+ ion, but also result in a large number of unstable metastables. Past reliance on free gadolinium tests to determine minimum synthesis duration and temperature guarantees the presence of unstable metastables.

Also, the macrocyclic amines tend to be more basic than the amines in a linear structure. For this reason, addition of the basic buffer (meglumine) if added before complete complexation can further destabilize the metastable forms. This is also a novel observation of the applicants not appreciated. Delay of meglumine addition until after verification of full complexification is critical to obtaining a stable GCA. In the literature, the base buffer is generally added with the uncomplexed gadolinium and ligand or before complete complexation.

There is also a practice of adding the meglumine during the Gd(dota)⁻ synthesis, before complete complexation, because early addition of base does catalyze the first step of metastable formation, but inhibits the second step of deprotonation to the final coordination complex. As a consequence of early addition of base, the protons left in the macrocyclic cavity's first coordination sphere are blocked from dissociation from the amine, which is required for the Gd3+ ion to be fully complex. Thus, reaction time without base addition becomes a critical parameter required to fully form the thermodynamically stable product, Gd(dota)⁻.

Even when the base is not added before full complexation, the complexation process is longer for the macrocyclic compared to the linear ligand. Experience with linear GCA has traditionally biased synthetic methods toward producing unstable macrocyclic GCAs. Noting that the probability for the Gd3+ ion to find a ligand drops with time as ligand is consumed, it is important to continue the synthesis even after the Gd3+ ion is proximal to a ligand molecule because the reaction completion rate once the Gd3+ ion is proximal to the ligand is on the order of many minutes to a few additional hours, depending upon pH. Increasing the pH prematurely, adding base, essentially ensures formation of metastables. It should be appreciated that the reaction rate is roughly proportional to the probability of complexation.

It is worth noting that a 1% presence by weight of metastables in a drug product equates to 10,000 ppm, well above the usual 10-100 ppm limit.

The stability of Gd-ligand complexes strongly impacts toxicity. The thermodynamic stability of a complex simply describes the concentrations of all species present in solution at equilibrium. Inspection of the thermodynamic stability equation reveals that the Gibbs free energy of the equilibrium process will have a large favorable entropy term due to release of seven of the eight first coordination sphere water molecules from the Gd3+. Metastable complexes, where fewer than seven first coordination sphere water molecules are expelled are proportionally less stable.

The variability of the entropy contribution is unique to macrocyclic GCAs, and is a novel insight of the present disclosure. The present disclosure maximizes the entropic contribution which in turn minimizes the GCA toxicity.

Also, the metal ion-ligand interaction has a large electrostatic component that contributes an additional favorable enthalpy term so the overall free energy change becomes quite favorable. This electrostatic component is compromised when the base is added before full complexation. Generally, the enthalpy term is reduced by the presence of extra first coordination sphere water molecules.

In general, the Gd3+ aqua ion is blocked from forming the most stable complex with a ligand using the methods of the present disclosure. Indeed, the testing methods which are employed to assess complex safety cannot detect the presence of unstable metastable complex forms. Consequently, new testing methods capable of detecting the presence of metastable complex forms are needed.

Another novel insight comes from the observation that the ligand molecules with the greatest stability are molecules with strongly basic groups in the otherwise acidic ligand. This is the reason why ligands with the highest stability always contain strongly basic amine groups. Second, linear amines are typically less basic than macrocyclic amines. For example, amine groups with amide-containing side-chains (DTPA-BMA and DOTA-(gly)4) are considerably less basic and stable compared to amine groups with acetate side-chains (DTPA and DOTA). The attractiveness of these basic groups are reduced when the reaction or resulting metastables are in a basic solution of meglumine buffer. Thus, the early addition of meglumine interferes with the advantage provided by strongly basic groups on the ligand.

These insights and the underlying chemical dynamics have a significant impact on the thermodynamic stabilities of the resulting macrocyclic Gd-ligand complexes. Relatively small variations in the reaction constants of the values for the ligand and Gd3+ ion results in large variation of the stability of the resulting complex. For typical reaction conditions, the complex stability can vary by over 10 orders of magnitude, with the metastables representing the least stable complex forms.

Proof that the standard art does not create GCAs with maximum stability, i.e., contain metastables, can be found by comparing the theoretical expected free gadolinium using the rate equation to the actual measured values of commercial products stored in bottles. One should recognize the primary destabilizing factor is the presence of calcium ion when injected into the bloodstream. The actual instability is likely many orders greater than the measured free gadolinium in the bottle. For example, the theoretical free gadolinium based on the rate equation for Gd-DOTA is 69 Gd3+ ions in 100 ml of GCA product, whereas the in-bottle measured value is on the order of $10^{13}$ Gd3+ ions in 100 ml of GCA product.

The difference can be explained in terms of the stability equation. The stability constants used in the equation are the values for fully complexed GCA. If one were to use the stability constants for the metastable forms, one would get far more Gd3+ ions theoretically. As few as 10 ppm metastable forms explains the discrepancy between measured and theoretical free gadolinium ion content.

The theoretical calculation contains assumptions about how many protonation constants to include for a given ligand. Nevertheless, drug manufacturers rely on this equation to assess a particular GCA's toxicity. The stability equation is likely a good relative measure for comparing the safety of linear GCAs because linear complexes do not have metastable forms. But the reliability of this relative measure breaks down for incompletely complex macrocyclic GCAs.

Even though linear complexes with gadolinium do not readily form metastable states, the linear complexes are dynamically less stable than the macrocyclic forms. Considering all the stability variables, the macrocyclic complexes yield less free gadolinium upon injection if the metastable complexes are driven to full chelation during synthesis of the drug product.

The Gd-DOTA complex is particularly susceptible to metastable complex formation due to the strong basicity of the donor groups of DOTA. Basicity determines the affinity for protons, and positively charged ions such as Gd3+. When the Gd-DOTA GCA is fully complexed it is entirely deprotonated. However, at physiological pH values, the ligand will be partially protonated. Because DOTA is a strongly basic ligand, there is strong competition for protons at pH 7.4. The basicity which gives a higher stability for the fully complexed form, also promotes metastable formation during synthesis and liberation of free ions in the body.

Experimentally, the stability was found to be 7 orders of magnitude lower for Gd-DOTA at pH 7.4. Ironically, Gd-DTPA has a more favorable binding constant than does Gd-DOTA at pH 7.4. For less basic ligands like Gd-DTPA-BMA and DOTA-(gly)4, the experimental values are closer to the theoretical thermodynamic stability constant because there is less competition from available protons at pH 7.4.

One can expect a macrocyclic GCA with metastable forms will release in the body far more Gd3+ ion than fully complexed macrocyclic GCA. In biological media there are competitors more active than protons. For instance endogenous ions like zinc, copper, and iron form very stable complexes with these ligands. Gadolinium also has a high affinity for phosphate, citrate, and carbonate ions and will bind to proteins like serum albumin.

There is a belief in chemistry which states that in microscopically reversible states, such as Gd3+ complexes, the mechanism in one direction is exactly the reverse of the mechanism in the reverse direction. One expects the rate of complex formation should approximate the rate of complex dissociation.

The most important chemical feature that determines the toxicity of Gd-complexes is the rate of dissociation of the complex in vivo. It follows, a short synthesis time equates with a complex with a fast dissociation rate. The reduction of the synthesis time based on a free gadolinium test practically guarantees the formation of metastables which are inherently unstable, and thus are quick to dissociate. This increases the probability of transmetallation, which blocks the gd3+ ion from re-complexing with the ligand, and increases the amount of free Gd3+ ion in the body.

It is important to match the elimination time in the body to the dissociation time of the chelate. Elimination time in the body is less than 2 hours, which is comparable to the complete complex formation time. Note, the complex must dissociate many times before the Gd3+ ion is replaced by a body constituent. The reason for this is that the time between dissociation and reassociation is short, and the gadolinium does not travel far from the ligand.

The applicants have empirically determined that synthesis time must be longer than the elimination time by at least a factor of 3, depending on the ligand. The reason for this factor is that the Gd3+ ion and ligand must first come in close proximity and maintain that proximity for the chelation time, hence the time to close approach must be added to the chelation time. One also must factor in the fact that the probability of close approach decreases as ligand is consumed. Hence, the usual synthesis time of 3 to 6 hours is grossly inadequate.

While wishing not to be bound to theory, the following encapsulates the motivation for the innovations presented in this application. Complexation of a lanthanide ion M by a polyaza polycarboxylic ligand L can take place in two ways. One reaction path comprises Equations (1) and (2) and the other path comprises Equations (1) and (3). The reaction paths involve metastable complexes (ML)* and final fully complexed form ML given by:

$$M+L \rightarrow (ML)^* \quad (1)$$

$$(ML)^* \rightarrow ML \quad (2)$$

$$M+L \rightarrow ML \quad (3)$$

It is important to appreciate that there are many metastable complex forms (ML)*, some of which participate in reaction pathway A given by Equations (1) and (2), and others participate in reaction pathway B given by Equations (1) and (3).

Note, the metastable species created in pathway B are unable to evolve into the final chelate ML. It is preferable to bias the synthesis to pathway A to avoid the formation of persistent metastables that must be removed. Therefore, it is desirable to employ methods which can eliminate the persistent metastables because there is no way to block pathway B completely.

Even when pathway A occurs predominantly, early termination of synthesis prevents the process given by Equation (2) to convert all the metastables to the fully chelated form.

Considering pathway A, three series of successive complexes are characterized by 1) the immediate $[LnH_n(dota)]^{(n-1)+**}$, 2) the metastable $[LnH_n(dota)]^{(n-1)+*}$, and 3) fully complexed $Ln(dota)^-$ complex, where 0 n 2 is the number of protons bonded to the ligand. The complexation mechanism involves three steps.

The $[LnH_n(dota)]^{(n-1)+**}$ complexes are rapidly formed, and are responsible for the premature "no free Gd3+ ion" result obtained by xylenol orange titration. This metastable has the lanthanide bound to four oxygen atoms of the carboxylate groups and to five water molecules. Subsequent heat moves the lanthanide into the macrocycle cavity, two new bonds are formed with two nitrogen atoms diametrically opposed in the tetraaza cycle and only three water molecules remain bound to the lanthanide in the metastable $[LnH_n(dota)]^{(n-1)+*}$ (0≤n≤2) complexes.

Further heating generates a concerted rearrangement which leads to the formation of thermodynamically stable $[Ln(dota)]^-$ complexes in which the lanthanide is bound to four nitrogen atoms, four carboxylate oxygen atoms, and one water molecule.

Figure 4:
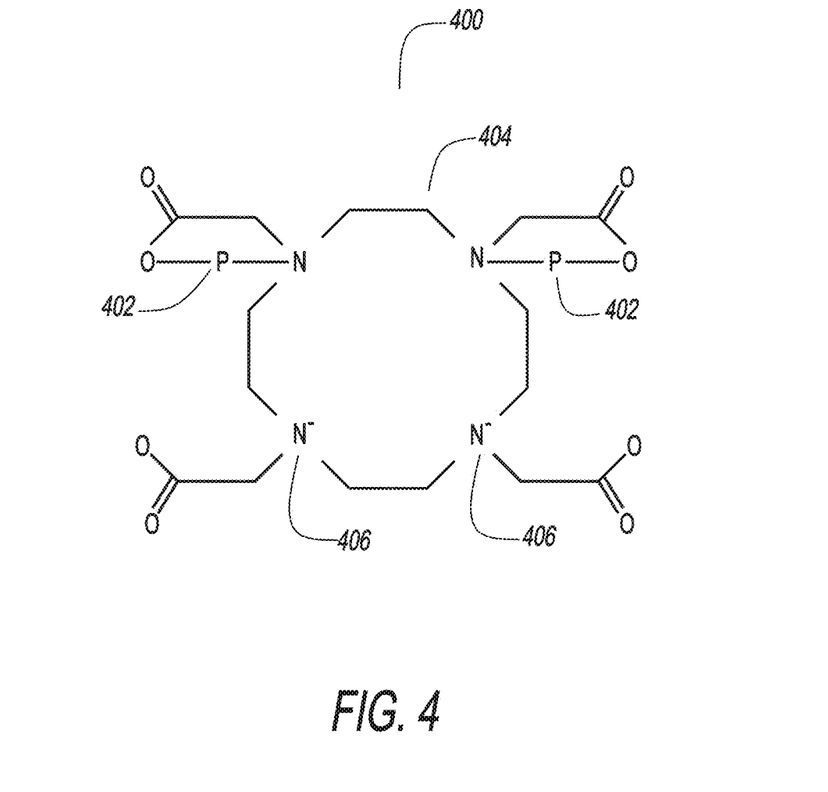
FIG. 4 depicts the hydrated ligand H2DOTA2−.

The energetically favored free ligand structures are $H_6DOTA^{2+}$ and $H_2DOTA^{2-}$. Referring to FIG. 4, the hydrate ligand $H_2DOTA^{2-}$ 400 comprises two protons 402 and DOTA ligand 404. The ligand has a total charge-2 given by the two amine nitrogens 406.

Both structures have very similar backbone conformations, i.e., all four carboxymethyl groups point to the same direction relative to the plane formed by the four nitrogen atoms of the macrocyclic ring and maintain a syn configuration. The coordinated DOTA ligand structure is similar to that of the free form and, therefore, is preorganized for complexation.

Therefore, it is reasonable to expect pathway A to predominate with the formation of the metastable $[Gd-H_2(dota)]^+$ with the four carboxylates in the syn configuration, it probably means that its formation requires ligand rearrangement. This is consistent with the fact that the preorganized $H_2DOTA$ with the four carboxylate arms pointing to the same side forms a more stable metastable.

Figure 5:
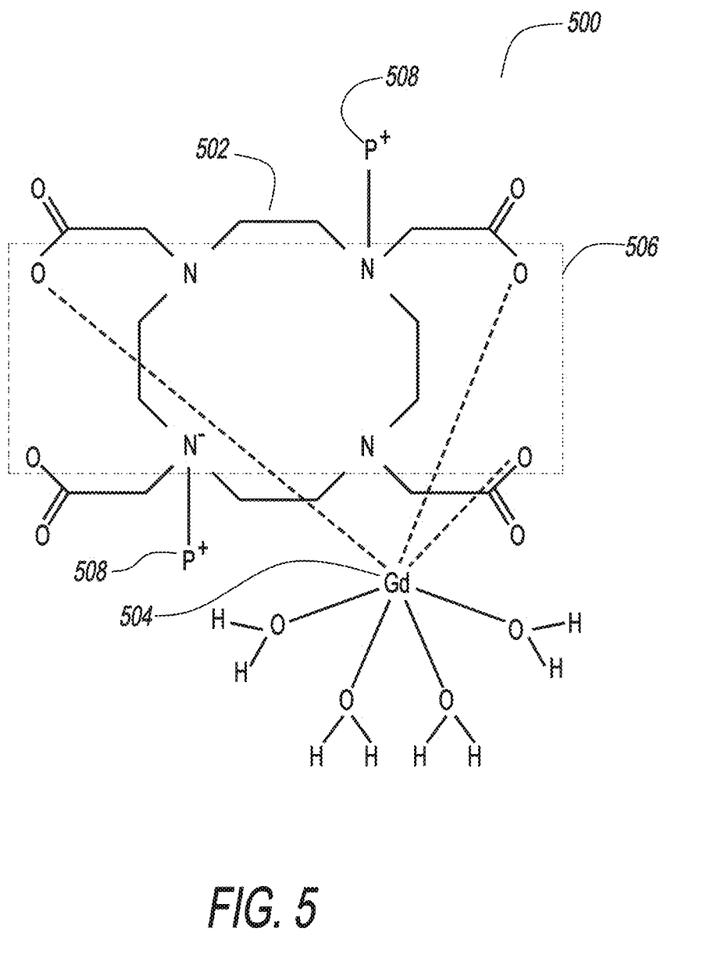
FIG. 5 depicts the metastable complex [Gd—H2(dota)]+.

Referring to FIG. 5, the metastable $[Gd-H_2(dota)]^+$ 500 comprises ligand 502 and Gd3+ ion 504. Note the Gd+ ion 504 is outside the first coordination sphere 506. The two protons 508 must be dissociated in order for the final coordinate complex to be obtained.

The long lived $[Gd-H_2(dota)]^+$ metastable has protons at two ring nitrogen atoms trans to each other. It does not have the Gd3+ ion in the cage determined by the four ring nitrogen and four acetate oxygen atoms (C=O); rather it is coordinated only by four acetate oxygen atoms on the side away from the plane of the macrocyclic ring because of the repulsion between Gd3+ ion and the ring protons. One expects $[Gd-H_2(dota)]^+$ to be in equilibrium with $[Gd-H(dota)]$ because these two species have conformally similar structures.

In the final rate-determining step, the metal ion (Gd3+) enters into the fully coordinated complex simultaneously with a thermodynamically driven deprotonation of the $[Gd-H(dota)]$ or $[Gd-H_2(dota)]^+$ metastables.

On the other hand, it is also possible the primary metastable leading to the final complex is the singly protonated GdH(dota) or triacetate derivatives of DOTA with the proton on a ring nitrogen. This metastable would have Gd3+ coordinated to at least one nitrogen in addition to the three carboxylate oxygens (C—O).

It is tempting to think the path to full complexation is just a matter of stripping off water molecules from the metastable complex. However, there is also considerable conformational change. For example, it is well-known that there are two isomers of the final complex $Gd(dota)^-$ that are observed in solution and in the crystalline form.

The major isomer M has the regular antiprism geometry and the minor isomer m has the inverted antiprism geometry, both with $C_4$ symmetry. These isomers differ in the orientation (helicity) of the carboxylate arms but have the same conformation of the tetraaza cycles. The energy difference between M and m is a few kilocalories per mole, but the barrier of interconversion from M to m is quite high. For example, in the case of Gd(dota)—complex, M is more stable than m by 4.3 kcal/mol, and the experimental barrier of interconversion from m to M is 22 kcal/mol.

From an energy barrier point of view, the final deprotonation is the rate limiting step. The energy barrier amounts to a proton transfer from NH to COO. The proton on the ring nitrogen is located inside the cage and is not accessible to outside base (OH⁻). To expose the proton to the outside base, the cage structure must open to form 3- or 2-coordinate conformations. The energy cost is considerable. This high energy barrier for exposing the proton is consistent with the rate-determining step being removal of the proton, and explains the unusually slow formation of $Gd(dota)^-$ complex and the existence of unusually stable metastables.

The mechanism of proton removal from the metastables and the energy barrier of this deprotonation process remain open questions. Two possible pathways for deprotonation of the metastables are: 1) insertion hydroxide into the cage, and 2) nitrogen inversion.

Here is proposed a novel thermodynamic mechanism which informs the method of the present disclosure. In the practice of the present disclosure, the proton is transferred from the ring nitrogen to the carboxylate oxygen by thermalization of the proton. The Gd3+ moves toward the ring in the spontaneous and concerted manner to form the octadentate coordination complex. The proton attached to the carboxylate group will be removed very fast by outside hydroxyl groups to form the final Gd(dota)− complex.

The energy barrier is lower than the energy cost needed to expose the ring proton by changing the conformation. Once the proton transfer occurs to form Gd(dota-H) (at moderate energy cost), the formation of the final Gd(dota)− complex is quite favorable because there is little conformational change required in the DOTA.

Deprotonation involves moving the proton from the inner (first) coordination sphere to the second coordination sphere.

While the loss of the proton enables the formation of the final Gd(dota)− complex, the most stable form of all the complexes, ironically the association of the Gd3+ ion to the DOTA likely decreases the metastable stability. For example, the replacement of one negatively charged carboxylate group of DOTA with a neutral amide group is known to significantly reduce the overall affinity of the ligand for lanthanide Ln3+ ions. Moving the proton from the inner nitrogen atom to the outer negatively charged carboxylate group destabilizes the complex transiently until the final complex is formed.

The enabling insight is that the minimum energy complex is the Gd(dota)− complex. The path to this stable complex involves a random sequence of metastable formations, some of which are sufficiently unstable to randomly move away from the desired final Gd(dota)− form, but given enough time, there is only one final state.

It is the instability of the metastables that allows Path B metastables to be transformed into Path A metastables. Time, temperature and proper detection are critical in obtaining a drug product of ultra-low free gadolinium potential. One refers to free gadolinium potential because these metastables are not free gadolinium, but they readily destabilize in seconds in vivo generating free Gd3+ ion, whereas the Gd(dota)− complex takes hours to dissociate in vivo. The dissociation time is comparable to the elimination time in the body.

Consequently, the presence of free gadolinium in a GCA outside the body (in the bottle) is indicative of the presence of metastables. While metastables have a low probability to dissociate into Gd3+ in the bottle, the Gd(dota)− complex has practically a zero probability to dissociate in the bottle. If the theoretical calculations are to serve as a guide, then the free Gd3+ concentration in the bottle should be well below 1 ppb, whereas free Gd3+ in commercial macrocyclic GCAs is measured between 1 and 100 ppm.

DETAILED DESCRIPTION OF THE DISCLOSURE

The present disclosure is a novel class of macrocyclic GCAs, and associated synthesis methods, where the metal ion is chosen from the lanthanide series and the coordination ligand has macrocyclic structure. The lanthanide series of chemical elements comprises the 15 metallic chemical elements with atomic numbers 57-71, from lanthanum through lutetium.

Here, the chemical symbol Ln is used in general to indicate lanthanide chemistry. All but one of the lanthanides are f-block elements, corresponding to the filling of the 4f electron shell. All lanthanide elements form trivalent cations, Ln3+, whose chemistry is largely determined by the ionic radius, which decreases steadily from lanthanum to lutetium Methods to Quantify Metastable States Laser excitation spectra of the transition of F D electrons of Gd3+ in the presence of ligands can be used to quantify complexation metastables and final product. It is known laser excitation at 577-581 nm, emission at 614 nm, is useful in detecting the $^5D_0 \rightarrow {}^7F_2$ transition.

During the process of complexation, the initial association of Gd3+ with DOTA and the final formation of Gd(dota) result in different ligand coordination fields and therefore different excitation spectra. The complexation reaction between Gd3+ and DOTA involves the following three steps. The first step is a fast equilibrium; the second and/or the third deprotonation reaction is considered rate-determining. Good excitation spectra can be obtained from 0.2 mM Gd3+(dota) solution at pH 6.10. To verify stability, the excitation spectra of a 0.2 mM Gd3+(dota) solution (pH 6.10) prepared and stored for 200 h and a solution freshly prepared by titrating a an acidic 0.2 mM Gd3+(dota) solution with (CH3)4NOH to pH 9.90 were compared. If the two spectra are the same, the reaction product is stable.

A simple inline test to evaluate how quickly Gd3+ is released from any chelated form is simply to add the complex to strong acid (0.1 M HCl) and measure the appearance of Gd3+ with time. The method can be modified by the addition of calcium or zinc ion, or the use of a synthetic blood serum preparation.

The relative kinetic stability of multiple runs of GCA batches is to expose the GCA to a solution containing phosphate anions at physiological pH. Even chelates with very high thermodynamic stability constants will equilibrate to form some free chelate and non-chelated gadolinium. Since gadolinium phosphate is insoluble, any non-chelated gadolinium will precipitate as insoluble gadolinium phosphate.

The detection system is to react according to Le Chatelier's Principle to establish a new equilibrium to replenish the "free gadolinium" until the phosphate anions are almost all precipitated from the solution. The rate at which this happens is determined by the rate of dissociation of Gd3+ from each metastable complex. Metastable complexes will have relatively high thermodynamic instability and a relatively fast rate of dissociation.

Removing Metastables

The phosphate precipitation can be used in the synthesis process, since the metastables can be completely dissociated and the free gadolinium removed by filtration.

Synthesis Methods

Up date previous process with metastable detection, meglumine titration, and pH control Examples of Macrocyclic GCAs with Reduced Metastables Example 1: Metastable-Free Gd-Dota Synthesis Preparation of DOTA Solution
1. Heat reactor to 25-30° C.
2. Charge water with DOTA
3. Begin stirring (stir unless otherwise indicated, nominal rate 300 rpm)
4. Charge 10% of the DOTA
5. Stir until uniformly distributed in the water
6. If all the DOTA is charged, then go to step 8
7. Go to step 4
8. Stir 10 min
Preparation of Gadolinium: DOTA Complex
9. Charge 25% by weight of the Gadolinium oxide
10. Stir until uniformly distributed
11. If all the Gadolinium oxide is charged then go to step 13
12. Go to step 9
13. Stir 10 min
14. Raise temperature to 95+/−2° C.
15. Stir 3 hrs.
16. Check clarity
17. If not clear continue for 1 hr, go to step 16 (this step took about 12 hours)
18. If clear, continue 1 hr and then cool to 40-45° C.
19. If precipitate forms, heat to 95+/−2° C. and stir for 1 hr, go to step 16
Verify Gd-Dota is Metastable-Free
20. A standard metastable-free Gd-dota reference solution is obtained by taking 5 ml of reactant obtained from steps 1-19 and diluting to a 0.2 mM Gd-dota solution.

One measures the metastable content after synthesis for 5, 10, 15, 20, 25, 30, and 35 hours, or until the concentration of the metastable asymptotes as close to zero as possible.

The metastable content is measured by placing a 5 ml Gd-dota solution titrated with meglumine to pH 6.10 in a square 10 ml quartz vessel. The output from a copper vapor laser tuned to 578.2 nm (Oxford Lasers, Didcot, United Kingdom) is directed through the reactant and the excitation spectrum obtained at 578.2 nm. Baseline is established by directing the laser through the quartz vessel filled with distilled water. A graph of excitation intensity (measured in millivolts) vs reaction time is plotted, and the reference solution obtained after the slope of this plot is less than 0.01 or the absorption intensity does not change by more than 1 between 5 hour reaction intervals.

The stability of the reference solution can be verified by checking that the excitation spectra of a 0.2 mM Gd-dota solution (pH 6.10) does not change after storing for 200 h at 20° C.

Once the reference solution is prepared, then product runs can be indexed against this standard.

If inline monitoring of metastable presence is desired, the reactant can be titrated with a strong acid (0.1 M HCl) and the free Gd3+ ion quantified by xylenol orange titration. The metastable will release free Gd3+ more quickly than fully complexed Gd-dota. The presence of multiple metastable forms can be detected by dynamic titration over the span of an hour or more, and calculating the Gd3+ ion as a function of time.

In addition, the relative kinetic stability of a Gd-dota complex is accessed by exposing the solution to phosphate anions at physiological pH. Even chelates with very high thermodynamic stability constants will equilibrate to form some free chelate and non-chelated gadolinium. Since gadolinium phosphate is insoluble, any non-chelated gadolinium will precipitate as insoluble gadolinium phosphate, and the free Gd3+ ion can be quantified by weighing the precipitate.

Verify Complex Formation
21. Verify absence of free gadolinium using Xylenol orange
22. If free gadolinium detected, add X DOTA, raise temperature to 95+/−2° C., stir for 1 hr and proceed to step 16
23. If not, proceed to step 23
Preparation of Gadoteric Acid Meglumine Solution
24. Add 90% of the meglumine at 40-45° C.
25. Sir 10 minutes
26. Measure pH-inline probe calibrated to 25° C. (USP)
27. If pH is >7.5, discard
28. If pH is between 7.0 and 7.5, then go to step 29
29. If pH <than 7.0, add 2% of the Meglumine, go to step 24
30. Stir for 1 hr at 40-45° C.
31. Check solution is clear, if yes proceed to 31, if not repeat 29
Gadoteric Acid Meglumine Solution Filtration
32. Cool the solution to 20-25° C.
33. Filter the solution using the carbon filter
34. Rinse the reactor with 20-25° C. water using ¼ V
35. Pass rinse through the filter
36. Repeat rinse steps 33 & 34 for a total of 2 rinses
37. Place filtrate and rinses back in reactor
38. Stir at 25-30° C. for 10 min
39. Measure Free DOTA by HPLC
40. If Free DOTA is 0.01-0.06% ww proceed to 42
41. If Free DOTA <0.01% ww, add 0.03% ww equivalent of DOTA
42. Stir for ½ hr and go to step 38
43. Measure pH-inline probe calibrated to 25° C. (USP)
44. If pH is between 7.0 and 7.5, then go to step 45
45. If pH <7.0, add meglumine. Stir 10 min. Go to step 42.
46. Stir ½ hr.
47. Check solution is clear, if yes proceed to 47, if not repeat 45
Verify Purity
48. Measure Purity by HPLC
49. If individual impurity >0.05%, go to step 32
Final API Adjustments
50. Measure Free DOTA by HPLC
51. If Free DOTA >0.06% ww, repeat steps 32-42
52. If Free DOTA is 0.01-0.06% ww proceed to 55
53. If Free DOTA <0.01% ww, add 0.03% ww equivalent of DOTA
54. Stir ½ hr
55. Go to Step 49
56. Measure pH
57. If pH is 7.0-7.5, then go to step 53
58. If pH <7.0, add Meglumine. Stir 10 min. Go to step 55
Final API Testing
59. Perform full API testing: Gadolinium content; Meglumine Content; Assay; Water Content; Heavy Metals Example 2: Metastable-Free Gd-dota Synthesis If it is desired to minimize the synthesis time, then the metastables can be removed after step 20 or after step 59 of Example 1 using the phosphate precipitation method described in Example 1. The complete complexation of Gd-dota is a statistical process, and eliminating all the metastable complexes by synthesis, the intent of Example 1, can more than double the synthesis time. Therefore, it may be cost effective to terminate the synthesis in the incompletely complexed state, wherein greater than 90% of the Gd-dota complexes are fully complexed, then removal of the metastable forms by phosphate precipitation may be economically advantageous.

Example 3: Establishing Minimum Detection Levels

The ability to measure a minimum concentration of 1 ppm Gd3+ ion depends on being able to prepare a $10^{-6}$ molar solution of Gd3+ and a 1 molar solution of Xylenol orange to an accuracy of $10^{-6}$.

$$\frac{[Gd(III)]}{[XO]} \times 10^6 = \text{ppm } Gd(III)$$

[ . . . ] is the molar amount of Gd(III) or Xylenol Orange (XO). In terms of spectral measurement $$\frac{Abs^{573}}{Abs^{573} + Abs^{433}} \times 10^6 = \text{ppm } Gd(III)$$

Ten 1 ppm Gd(III) ion solutions were titrated to 7.0+/−0.1 pH with NaOH and the ammonia removed by vacuum.

|  | 1 ppm | 10 ppm | 100 ppm | 1000 ppm | 10,000 ppm | 100,000 ppm |
| --- | --- | --- | --- | --- | --- | --- |
| Solution 1 | 5.6 +/− 0.6 | 14.8 +/− 0.6 | 93.7 +/− 0.7 | 1009.3 +/− 0.5 | 10,006.6 +/− 0.9 | 100,005.7 +/− 0.5 |
| Solution 2 | 3.1 +/− 0.7 | 17.0 +/− 0.4 | 95.5 +/− 0.6 | 992.8 +/− 0.5 | 10,009.3 +/− 0.8 | 99,993.1 +/− 0.3 |
| Solution 3 | 2.6 +/− 0.6 | 11.5 +/− 0.9 | 102.6 +/− 0.3 | 1005.6 +/− 0.7 | 9,996.8 +/− 0.2 | 99,998.9 +/− 0.0 |
| Solution 4 | 0.1 +/− 0.2 | 8.9 +/− 0.2 | 109.2 +/− 0.0 | 1009.7 +/− 0.5 | 9,991.6 +/− 0.3 | 99,991.8 +/− 0.3 |
| Solution 5 | 1.5 +/− 0.0 | 8.5 +/− 0.9 | 97.3 +/− 0.3 | 1006.5 +/− 0.8 | 10,006.3 +/− 0.4 | 99,993.1 +/− 0.5 |
| Solution 6 | 2.3 +/− 0.4 | 5.9 +/− 0.3 | 92.8 +/− 0.1 | 1001.9 +/− 0.6 | 10,002.4 +/− 0.0 | 99,995.8 +/− 0.7 |
| Solution 7 | 6.9 +/− 0.1 | 12.7 +/− 0.2 | 97.1 +/− 0.4 | 991.4 +/− 0.3 | 9,992.2 +/− 0.0 | 99,992.9 +/− 0.6 |
| Solution 8 | 4.9 +/− 0.0 | 4.9 +/− 0.0 | 92.5 +/− 0.9 | 1003.9 +/− 0.5 | 10,009.5 +/− 0.6 | 100,000.6 +/− 0.5 |
| Solution 9 | 0.7 +/− 0.1 | 10.6 +/− 0.7 | 103.6 +/− 0.0 | 994.0 +/− 0.1 | 10,002.8 +/− 0.9 | 100,002.1 +/− 0.5 |
| Solution 10 | 1.8 +/− 0.3 | 12.9 +/− 0.3 | 94.6 +/− 0.9 | 1007.9 +/− 0.4 | 10,003.7 +/− 0.4 | 99,995.3 +/− 0.5 |
| MEAN | 3.0 +/− 2.1 | 10.8 +/− 3.6 | 97.9 +/− 5.2 | 1002.3 +/− 6.7 | 10,002.1 +/− 6.2 | 99,996.9 +/− 4.4 |

(sdev result of integration of 10 spectrometer runs)

The Xylenol orange titration relies on a solution color change. Since the photon source used to assess color change will not be isomorphic in wavelength, one needs to calibrate the source and detector for each of the two wavelengths quantified in the xylenol orange method (see USP Memorandum on Gadolinium Contrast Agents). The calibration is only as good as the thermal stability of the source and detector. Therefore, it will be important to put source and detector into thermal equilibrium before measurement, therefore a 1 hour baseline must be established where the calibration varies by less than 10 ppm signal.

The entire measurement setup is to be placed in a thermally controlled environmental chamber at 20° C.

For these reasons, 10 separate 1 ppm Gd(III) solutions were prepared and equilibrated to 20° C. It is not sufficient to make one solution and take 10 measurements. Each of the 10 standard solutions are to be measured a minimum of 10 times, by performing a time integration until the variability reaches the 1 ppm threshold. This is possible by the programmable algorithm interface of commercial spectrometers.

The above procedure is to be repeated for 10 ppm solution and 100 ppm. Based on naive thermodynamic considerations, it is expected the robust (standard deviation less than 10%) detection range will start at between 10 ppm and 100 ppm.

Once the robust detection range is established, then the variability in decades is to be quantified: 1000 ppm, 10,000 ppm (1%), and 100,000 ppm (10%).

Calibration Results

The concentration of a solution of Gd(III) ion is determined stoichiometrically where the concentration is given by:

Example 4. Identification of Metastables in Incompletely Synthesized Complex Solution Using Example 1, metastable forms and free Gd3+ was quantified. 40.5 g of DOTA was suspended in 150 ml of water at a temperature of 75° C. 17.8 g of gadolinium oxide was added, and the batch was stirred at 75° C. for 2 hours. The solution that was produced was mixed with 19.5 g of meglumine and stirred at 75° C. for one hour. Then, the content of free DOTA, free gadolinium, and complex was determined, and the final content of excess free DOTA was set.

Five reactions were run, using 4.05 g of DOTA, 15 ml water, and 1.78 g of gadolinium oxide. Ten spectroscopic measurements using Xylenol orange were conducted. Here the calculation of ppm is different, where the amount of xylenol orange equals the number of theoretical drug molecules, that is for each gadolinium oxide molecule one will generate two gadolinium ions which can either complex with DOTA or remain free, accordingly [XO]=[GdO×2]. This is the molar amount of xylenol orange added to each reaction product. We one uses $$\frac{Abs^{573}}{Abs^{573} + Abs^{433}} \times 10^6 = \text{ppm } Gd(III)$$

Understanding that the denominator is a constant and $Abs^{573}$ is the number of free Gd(III) ions that react with the xylenol orange. This is a conservative measure of ppm, given by the ratio of free gadolinium and total gadolinium in the reactant ($\times 10^6$). Another possible definition, which would give a higher number (less conservative) is simply comparing free gadolinium to complexed gadolinium, which would mean ppm of free gadolinium for every million complexed gadolinium. The two definitions depart significantly at free gadolinium concentrations above 1%.

| Reaction # | Free Gd(III) |
| --- | --- |
| Reaction 1 | 30,415.3 +/− 4.4 |
| Reaction 2 | 19,567.6 +/− 3.5 |
| Reaction 3 | 22,989.0 +/− 0.6 |
| Reaction 4 | 36,080.7 +/− 3.8 |
| Reaction 5 | 45,890.4 +/− 7.6 |
| MEAN | 30,989 +/− 9410 ppm |

Example 5. Metastables as a Function of Reaction Time

Stoichiometric ratios of gadolinium oxide were reacted with DOTA according to the procedure outlined in Example 1. Measurements were taken (N=1) to conserve volume. The final measurement was performed 5 times.

| Hours of reaction | metastables [ppm] | |
| --- | --- | --- |
| 3 hours | 28,094 +/− 9.7 | N = 1 |
| 8 hours | 3,853 +/− 12.4 | N = 1 |
| 24 hours | 72 +/− 5.0 | N = 1 |
| 32 hours | 0.8 +/− 1.3 | N = 10 |

Now titrate with meglumine to pH 7.0

| | |
| --- | --- |
| 1.2 +/− 3.8 | N = 2 |

Example 5: Optimizing Contrast and Stability

Due to the low sensitivity of MRI as an imaging technique, large quantities of a contrast agent, often on the gram scale, must be injected into the patient to obtain useful images. The ability to reduce the quantity of GBCAs required is highly desirable, especially when considering the toxicity problems discussed above. One way in which the amount of contrast agent required can be reduced is to enhance its relaxivity.

Relaxivity is a measure of how water relaxation rate changes with concentration of a contrast agent, and high relaxivities are indicative of more effective agents. The greater the number of coordinated inner sphere water molecules the higher the complex relaxivity.

All existing clinical GBCAs are based on octadentate polyaminocarboxylate ligands. As trivalent gadolinium prefers a coordination number of 9, this leaves one available coordination site free for an inner sphere water molecule.

The hydration state of the complex can be increased by stopping the coordination process early so that metastables are formed by reducing the number of coordination sites devoted to the Gd3+ ion. Importantly though, this lowers the thermodynamic stability of the complex and renders the metal ion more accessible to endogenous anions.

This accessibility leads to demetallation of gadolinium (III) complexes in vivo, causing further toxicity issues. Many in the field have tried to master the subtle interplay between maximizing relaxivity through accessing higher hydration states and forfeiting thermodynamic stability and kinetic inertness.

This strategy is flawed, and one objective of this application is to achieve greater relaxivity without sacrificing complex inertness. The inventors have surprisingly found that chemical stability is clinically less important than complex inertness. Kinetic inertness indicates the rate of Gd3+ release, while thermodynamic stability describes how much Gd3+ is released at equilibrium under certain conditions. Since the rate at which equilibrium is reached for macrocyclic gadolinium (III) complexes in vivo is very slow and normally cannot be reached during their residence time, thermodynamic stability cannot accurately predict Gd3+ release for macrocyclic GBCAs. These inventors conclude that thermodynamic stability alone is insufficient to predict the in vivo dissociation of macrocyclic chelates.

This conclusion is based on the following observation. The complex [Gd(OH2)(dota)]− is somewhat thermodynamically stable but is more kinetically inert and results in low in vivo deposition; while [Gd(OH2)(dtpa)]2− is highly thermodynamically stable but has a low kinetic inertness and has had its use restricted.

The same complex with Gd3+ replaced by Eu3+ is much more kinetically inert, despite a much lower thermodynamic stability than (fully complexed) [Gd(OH2)(dota)]−. This combined information suggests that it is kinetic inertness rather than thermodynamic stability that appears to be the useful predictor of in vivo Gd3+ release from GBCAs. Maximizing kinetic inertness should be a critical concern for those seeking to develop future GBCAs.

In this embodiment, chemical inertness is enhanced so that the presence of metastables (higher hydration states) does not contribute to Gd3+ deposition in the body.

To understand the logic behind the present embodiment it is necessary to consider the solution behavior of lanthanide (III) complexes of dota. There are known to be four different stereoisomers of [Ln(dota)]− in solution, which arise from the orientation of the five-membered coordination metallacycles formed by ethylene bridges in the macrocycles λλλλ and δδδδ and the corresponding positions of the pendant arms $\wedge$ and $\Delta$.

In geometric terms, the shapes adopted by these stereoisomers are described as square antiprismatic (SAP) or twisted SAP (TSAP). Each of these isomers may be characterized by the twist angle between the nitrogen and oxygen donor atom planes. This angle varies according to which Ln3+ center the ligand is complexed to, but is typically around 40° for SAP structures and between −20° and −30° for TSAP geometries. The two SAP and two TSAP isomers are enantiomeric pairs, and interconversion between them is possible on the nuclear magnetic resonance (NMR) timescale, leading to the broadening often seen in proton NMR spectra of lanthanide (III) complexes of dota.

Interconversion occurs through two mechanisms: rotation of the acetate arms or inversion of the macrocyclic ring. In order to maximize complex inertness, it is imperative that interconversion is minimized. Chirality can be exploited to maximize complex inertness. Introduction of chirality to the macrocycle itself and the pendant arms can render both interconversion mechanisms unfavorable and cause the complex to favor a particular geometry, thus reducing kinetic lability of the complex.

The introduction of chirality locks ring conformation and facilitates ligand pre-organization during synthesis, resulting in greater complex inertness. Chirality has the added advantage of making the metastable forms far less likely to persist in the reaction, if at all.

The gadolinium (III) complexes comprising the present embodiment possess increased steric bulk resulting in a greater propensity for TSAP isomer formation, potentially due to steric clashes with the acetate arms rendering SAP geometry unfavorable. SAP geometry is associated with the more hydrate metastables.

Figure 6:
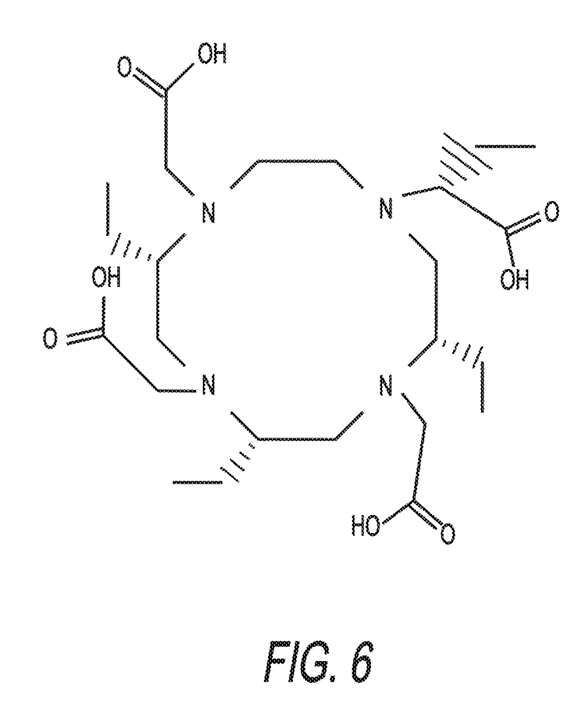
FIG. 6 illustrates tetraethyl-substituted ligand H4Et4dota.

For example, SAP and TSAP isomers of a Gd3+ complex of a tetraethyl-substituted ligand [$H_4$Et4dota], see FIG. 6. Analysis of rate equations of both isomers of the gadolinium (III) complex of $H_4$Et4dota have greater than 1 day persistence in the presence of 1000 equivalents of a strong competing chelate ($H_5$dtpa) and are expected to exhibit no demetallation after 100 h at 50° C. in the presence of a 100-fold excess of $ZnCl_2$. This theoretically remarkable kinetic inertness can be attributed to the influence of the chiral substituents which enhance complex rigidity, leading to the restricted and non-interconvertible SAP and TSAP structures. Based on calculation, it is the interconversion between SAP and SAP structures and not the structures themselves which reduces kinetic inertness.

Figure 7:
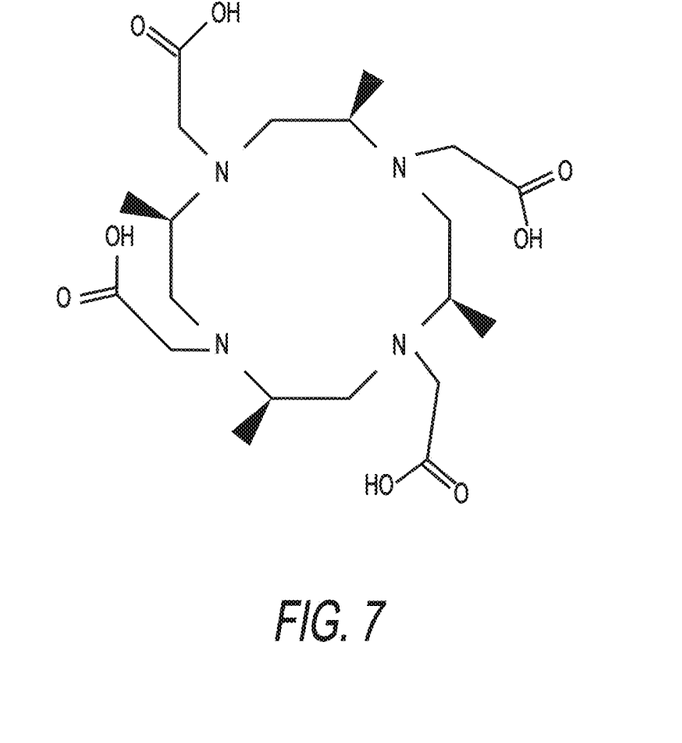
FIG. 7 illustrates tetramethyl substituted ligand H4Me4dota.
Figure 8:
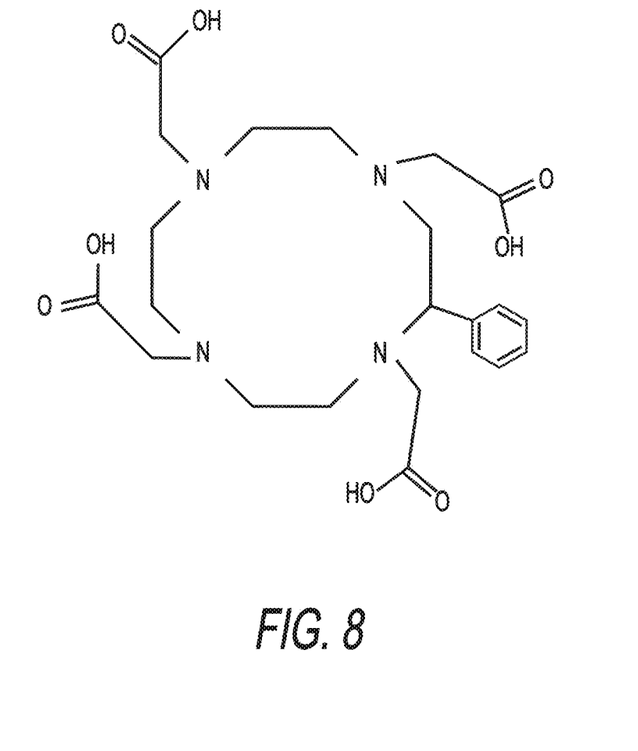
FIG. 8 illustrates phenyl-substituted ligand H4Phdota.
Figure 9:
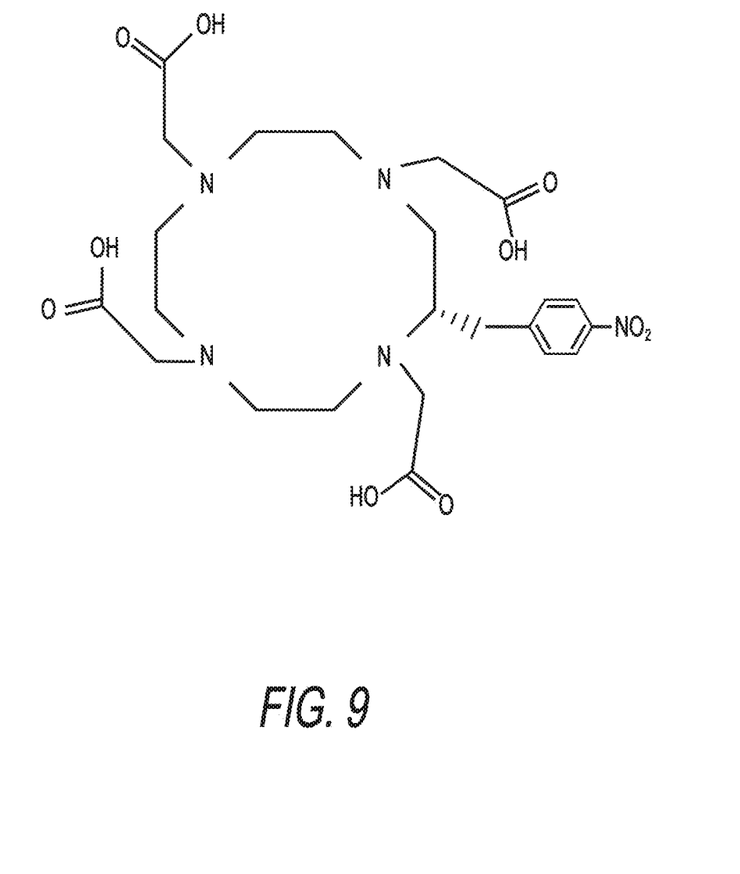
FIG. 9 illustrates nitrobenzyl-substituted ligand H4nbdota.

Chirality can be introduced by the examples given in FIGS. 6-9. FIG. 6 illustrates tetraethyl-substituted ligand $H_4$Et4dota. FIG. 7 illustrates tetramethyl substituted ligand $H_4$Me4dota. FIG. 8 illustrates phenyl-substituted ligand $H_4$Phdota. FIG. 9 illustrates nitrobenzyl-substituted ligand $H_4$nb-dota.

These chiral modifications to dota should have no effect on toxicity of the ligand and greatly reduce the Gd3+ toxicity of GBCA based on the chiral forms of dota.

Example 6: Free Gd3+ Results—Comparative Data

The contrast agents of the present disclosure were compared to a commercially available gadolinium-based contrast agents both in vitro and in vivo. After 30 minutes at standard dosing the contrast agents of the present disclosure released significantly less free GAD as summarized in the table below.

| GBCA | In Vitro PPM | In Vivo PPM |
| --- | --- | --- |
| Contrast agents of the present disclosure | 2.9 +/− 0.8 | 34.8 +/− 17 |
| DOTAREM ® (gadoterate meglumine) | 1,204 +/− 3.9 | 2.9 +/− 24 |
| | 415 times less free GAD | 256 times less free GAD |

The invention claimed is:

1. A lanthanide series contrast agent comprising:
an aqueous solution having a plurality of lanthanide macrocyclic chelate molecules dispersed therein, and meglumine;
wherein the lanthanide macrocyclic chelate molecules comprise metastable chelated molecules and fully chelated molecules, and wherein the number of said metastable chelated molecules is less than 10 molecules per million of said fully chelated molecules.

2. The lanthanide series contrast agent of claim 1, comprising gadolinium ion.

3. The lanthanide series contrast agent of claim 2, wherein the aqueous solution has Gd3+ ion content that is less than 1 part per million (ppm).

4. The lanthanide series contrast agent of claim 2, wherein the lanthanide series contrast agent exhibits a Gd3+ ion content after 30 minutes that is less than 10 ppm in a solution of 1% by weight of said lanthanide series contrast agent and 99% fresh bovine serum.

5. The lanthanide series contrast agent of claim 2, wherein the lanthanide series contrast agent exhibits a Gd3+ ion content after 60 minutes that is less than 100 ppm in a solution of 0.5 mmol/ml gadolinium chelate and equal parts 10% by weight ZnCl solution.

6. The lanthanide series contrast agent of claim 1, wherein the macrocyclic chelate molecules are DOTA.

7. The lanthanide series contrast agent of claim 6, comprising gadolinium ion.

8. The lanthanide series contrast agent of claim 1, comprising europium.

9. The lanthanide series contrast agent of claim 1, wherein the macrocyclic chelate molecules are triacetate derivatives of DOTA.

10. A method of making an aqueous solution having a plurality of lanthanide macrocyclic chelate molecules dispersed therein, wherein less than 10 said lanthanide macrocyclic chelate molecules per million have more than one water molecule in a first coordination sphere, the method comprising:
providing an aqueous solution having a plurality of the lanthanide macrocyclic chelate molecules dispersed therein, wherein the lanthanide macrocyclic chelate molecules comprise greater than 10 ppm of metastable lanthanide macrocyclic chelate molecules;
contacting the aqueous solution with an acid that precipitates greater than 90% of the metastable lanthanide macrocyclic chelate molecules from the aqueous solution, thereby form a mixture containing the precipitate and residual aqueous solution; and
separating at least a portion of the residual aqueous solution in the mixture from the precipitate.

11. The method of claim 10 wherein the precipitate is a lanthanide phosphate.

12. The method of claim 10, wherein the aqueous solution comprises gadolinium ion.

13. A method of enhancing a biologic image obtained on a subject by magnetic resonance imaging, the method comprising:
administering an effective amount of a lanthanide series contrast agent to the subject, the lanthanide series contrast agent comprising an aqueous solution having a plurality of lanthanide macrocyclic chelate molecules dispersed therein, and meglumine, wherein the lanthanide macrocyclic chelate molecules comprise metastable chelated molecules and fully chelated molecules, and wherein the number of said metastable chelated molecules is less than 10 molecules per million of said fully chelated molecules; and
obtaining an image by magnetic resonance imaging.

14. The method of claim 13, wherein the lanthanide series contrast agent comprises gadolinium ion.

* * * * *